(12) United States Patent
Ahuja et al.

(10) Patent No.: US 9,096,498 B2
(45) Date of Patent: Aug. 4, 2015

(54) CUCN-MEDIATED ONE POT PRODUCTION OF CINNAMONITRILE DERIVATIVES

(71) Applicant: Council of Scientific & Industrial Research, New Delhi (IN)

(72) Inventors: Brij Bhushan Ahuja, Pune (IN); Reddy S. Rekula, Pune (IN); Arumugam Sudalai, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/383,371

(22) PCT Filed: Mar. 7, 2013

(86) PCT No.: PCT/IN2013/000137
§ 371 (c)(1),
(2) Date: Sep. 5, 2014

(87) PCT Pub. No.: WO2013/132520
PCT Pub. Date: Sep. 12, 2013

(65) Prior Publication Data
US 2015/0031899 A1    Jan. 29, 2015

(30) Foreign Application Priority Data
Mar. 7, 2012   (IN) .............................. 664/DEL/2012

(51) Int. Cl.
| | | |
|---|---|---|
| C07D 317/44 | (2006.01) |
| C07C 255/00 | (2006.01) |
| C07C 253/14 | (2006.01) |
| C07D 317/58 | (2006.01) |
| C07C 255/34 | (2006.01) |
| C07D 317/60 | (2006.01) |
| C07C 303/30 | (2006.01) |
| C07C 319/20 | (2006.01) |
| C07D 317/68 | (2006.01) |

(52) U.S. Cl.
CPC ............. *C07C 253/14* (2013.01); *C07C 255/34* (2013.01); *C07C 303/30* (2013.01); *C07C 319/20* (2013.01); *C07D 317/58* (2013.01); *C07D 317/60* (2013.01); *C07D 317/68* (2013.01)

(58) Field of Classification Search
CPC ... C07D 317/58; C07D 317/60; C07C 255/34
USPC .......................................... 549/442; 558/401
See application file for complete search history.

(56) References Cited

FOREIGN PATENT DOCUMENTS

EP        0873306        *  7/1997  ............ C07C 253/10

OTHER PUBLICATIONS

M. Prochazka et al. "Preparation of Unsaturated Nitriles," Collection of the Czechoslovak Chemical Society, vol. 48, pp. 1765-1773, (1983).
Y. Sakakibari et al. "The Cyanation of Vinyl Halides with Alkali Cyanides Catalyzed by Nickel (0)-Phosphine Complexes Generated in Situ: Synthetic and Stereochemical Aspects," Bull. Chem. Soc. Jpn., 68, 3137-3143, (1995).
L. H. Li et al. "An Environmentally Benign Procedure for the Synthesis of Aryl and Arylvinyl Nitriles Assisted by Microwave in Ionic Liquid," Synlett, No. 13, 2094-2098, (2006).
International Search Report and Written Opinion of the International Searching Authority Dated Jul. 23, 2013.

* cited by examiner

*Primary Examiner* — Andrew D Kosar
*Assistant Examiner* — Raymond Covington
(74) *Attorney, Agent, or Firm* — Locke Lord LLP; Barry Kramer; Nicholas J. DiCeglie, Jr.

(57) ABSTRACT

The present invention discloses a cheaper and practical protocol for the construction of a wide variety of o-cyanocinnamonitrile and their structural analogs that proceeds with good yields in a single step using CuCN as the only reagent.

5 Claims, No Drawings

CUCN-MEDIATED ONE POT PRODUCTION OF CINNAMONITRILE DERIVATIVES

CROSS REFERENCE TO RELATED APPLICATIONS

This application is a 35 U.S.C. §371 National Phase Application of International PCT Patent Application No. PCT/IN2013/000137, filed Mar. 7, 2013 which application claims the benefit of priority to Indian Patent Application No. 664/DEL/2012, filed Mar. 7, 2012, the contents of each of which in their entirety are hereby incorporated herein by reference.

FIELD OF INVENTION

The present invention relates to a cheaper and practical protocol for the preparation of compounds of formula A, its isomers and their structural analogues in a one pot and single step via hydrocyanation reaction of compound of general formula I with good yields.

1) Rosenmund-von Braun Reaction:

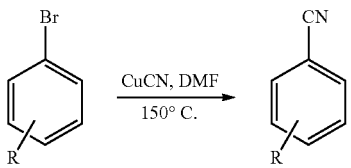

2) This Work:

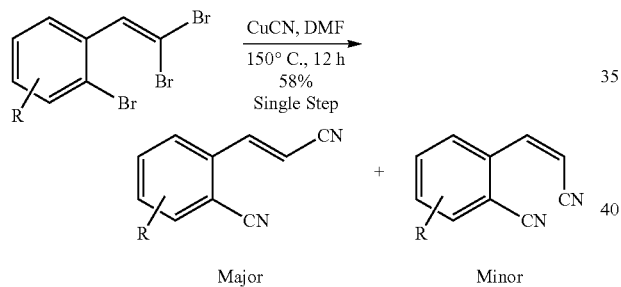

BACKGROUND OF INVENTION & DESCRIPTION OF PRIOR ART

Aryl nitriles can be prepared by the cyanation of aryl halides with an excess of copper(I) cyanide in a polar high-boiling solvent such as DMF, nitrobenzene, or pyridine at reflux temperature using Rosenmund-von Braun Reaction.

Alpha beta unsaturated nitriles are versatile reagents which have been used extensively in the synthesis of heterocycle compounds. Synthesis of cinnamonitrile by treating benzaldehyde with acetonitrile in presence of alkali is disclosed in Organic Syntheses, Coll. Vol. 7, p.108 (1990); Vol. 62, p.179 (1984). An article titled "Efficient One-Pot Synthesis of 2-Amino-4H-chromenes Catalyzed by Ferric Hydrogen Sulfate and Zr-Based Catalysts of FI" published in Synthesis and Reactivity in Inorganic, Metal-Organic, and Nano-Metal Chemistry, Volume 41, Issue 9, 2011, wherein, the preparation of α-cyanocinnamonitrile is carried by the condensation of aldehyde with malononitrile to afford α-cyanocinnamonitrile derivatives by Knoevenagel addition reaction.

Decarboxylation of E-3-phenyl-2-cyanopropenoic acid in dimethyl sulfoxide containing sodium bicarbonate, lithium chloride, and water in molar excess afforded, with high stereospecificity, Z-cinnamonitrile is disclosed in an article titled "Stereochemistry of the dealkoxycarbonylation of methyl α-cyanocinnamate and of the decarboxylation of the corresponding cyano acid: a facile stereoselective route to Z-cinnamonitrile" Tetrahedron Letters, Volume 24, Issue 36, 1983, Pages 3835-3838. Article titled, "HYDROCYANATION OF ALKENES AND ALKYNES" by T. V. (BABU) RAJANBABU reports that Hydrogen cyanide itself is relatively unreactive, but in the presence of a catalyst HCN adds to carbonyl compounds, alkenes, and alkynes, offering a direct and economical way to such organonitrile intermediates.

In a scientific article titled, "The preparation of aryl nitriles" by DIANDRA M. RUDZINSKI, NICHOLAS E. LEADBEATER in *chimica oggi/Chemistry Today*—vol. 29 n. 4 July/August 2011, reports the process of CYANATION through Modern methodologies by using catalytic amounts of transition-metal complexes, together with less toxic cyanide sources making chemistry more efficient, applicable and safer.

Scheme 1. Historical perspective on the cyanation of aryl halides-
(a) Rosenmund; (b) Pongrantz; (c) von Braun

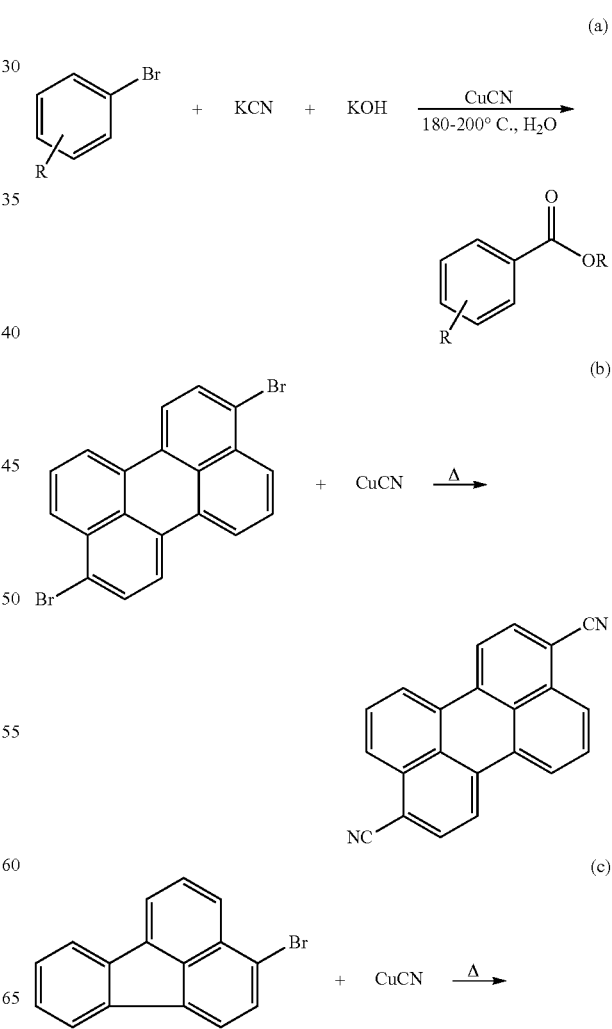

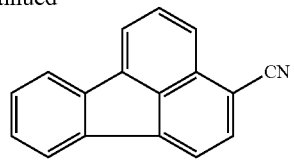

Scheme 4. Nickel-mediated cyanation and tandem halide exchange/cyanation approach to the conversion of aryl halides to nitriles.

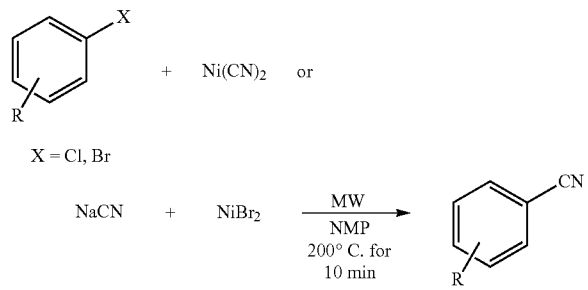

Scheme 6. Use of Cu2Fe(CN)6 as both catalyst and cyanide source for cyanation of aryl halides.

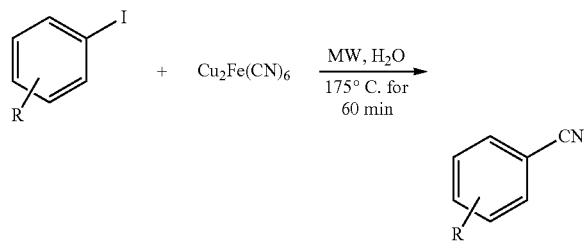

Article titled, "Mechanistic Insights into the Hydrocyanation Reaction" by Laura Bini in page 121, reports the hydrocyanation of styrene in presence of CuCN giving 78% conversion and 88% selectivity with a ratio of 13:87 for linear and branched nitriles and a yield of 73-80%. cinnamonitrile and their esters have wide range of industrial applications for example in cosmetic industry.

Although few inventions have been made in the synthesis of cinnamonitrile they require multiple steps with consumption of large quantities of hazardous chemicals with less efficiency and narrow substrate scope. Therefore, there is a need in the art to provide an alternate and effective synthesis to provide a library of cinnamonitrile. Further it would be desirable have a process of synthesis of cinnamonitriles by a convenient single step one pot process. Specifically, it would be desirable to provide a simple process for the conversion of dibromovinyl benzenes to their corresponding cinnamonitriles.

OBJECTS OF INVENTION

The main object of the present invention is to provide an effective one pot synthesis, single step for the preparation of cinnamonitrile derivatives via hydrocyanation reaction with good yields.

SUMMARY OF INVENTION

In an embodiment of the present invention a one pot, single step process for the preparation of compound of formula A and its isomers, starting from compounds of formula I,

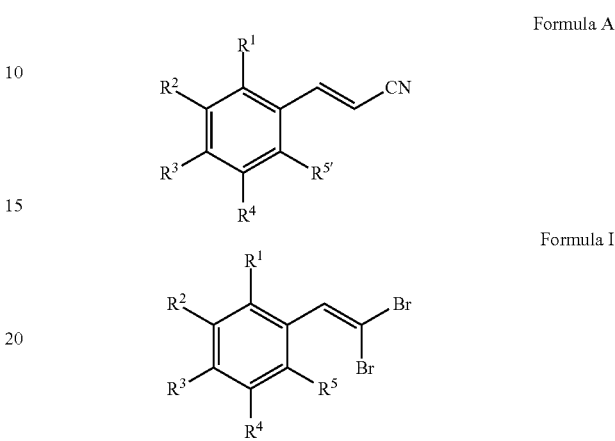

Wherein,
$R^1$ is hydrogen;
$R^2$ is selected from H, OMe, OTs, OBn;
$R^3$ is selected from H, OMe, OTs, OBn, $NO_2$;
$R^4$ is selected from H, OMe, F;
$R^5$ is selected from H, NO2, BR;
$R^{5'}$ is selected from H, NO2, CN;
$R^2$ and $R^3$ can together be selected as —O—$CH_2$—O—;
comprising the steps of reacting compound of formula I with CuCN in DMF, under reflux in presence of $N_2$ atmosphere to obtain the desired compound of formula A in the range of 50-90% yield.

In another embodiment of the present invention, the said compound of formula I and CuCN are in the ratio of 1:2 to 1:3.

In yet another embodiment of the present invention, isomers of compound of formula A are trans and cis isomers in the ratio of 3:1 to 10:1.

In yet another embodiment of the present invention, the reaction is carried out at a temperature ranging from 140 to 160° C.

In yet another embodiment of the present invention, the reaction is carried out for a time ranging from 10 to 15 hours.

DETAILED DESCRIPTION OF THE INVENTION

In accordance with the above, the instant invention provides one pot single step synthesis, of CuCN-mediated hydrocyanation reaction, for the preparation of cinnamonitrile derivatives. The CuCN-mediated hydrocyanation reaction according to the invention essentially makes use of the conditions prescribed for Rosenmund-von Braun Reaction.

The process of the present invention is easier to adopt on industrial scale for preparation of library of cinnamonitrile derivatives as it involves a one pot hydrocyanation reaction. The process of the instant invention is cost effective when compared to the existing methods as it involves CuCN, a very cheaper reagent, easy to maintain and perform at higher scales, showed remarkably broad substrate scope and good functional group tolerance and do not cause much effluent generation. The procedure tolerates a series of functional groups, such as methoxyl, fluoro etc.

In an aspect of the invention, cinnamonitrile derivative of formula (A) is represented as enlisted herein:

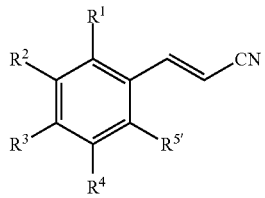

Formula A

Wherein,
R$^1$ is hydrogen;
R$^2$ is selected from H, OMe, OTs, OBn; (Ts=Tosyl, Bn=Benzyn))
R$^3$ is selected from H, OMe, OTs, Obn, NO$_2$;
R$^4$ is selected from H, OMe, F;
R$^{5'}$ is selected from H, NO2, CN;
R$^2$ and R$^3$ can together be selected as —O—CH$_2$—O—;
In an aspect of the invention, the compound of Formula I is

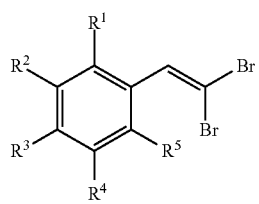

Formula I

Wherein,
R$^1$ is hydrogen;
R$^2$ is selected from H, OMe, OTs, OBn;
R$^3$ is selected from H, OMe, OTs, OBn, NO$_2$;
R$^4$ is selected from H, OMe, F;
R$^5$ is selected from H, NO2, BR;
R$^2$ and R$^3$ can together be selected as —O—CH$_2$—O—;

In a preferred embodiment, the invention discloses preparation of cinnamonitrile derivatives, which process comprises treating substituted 2,2-dibromovinyl benzene with CuCN in DMF at 150° C. for 10-15 hrs to obtain substituted cinnamonitrile derivative in a single step. The bromo vinyl benzene and CuCN are used in the ratio of 1:2 to 1:3 in the process described herein. The reaction is shown in scheme below:

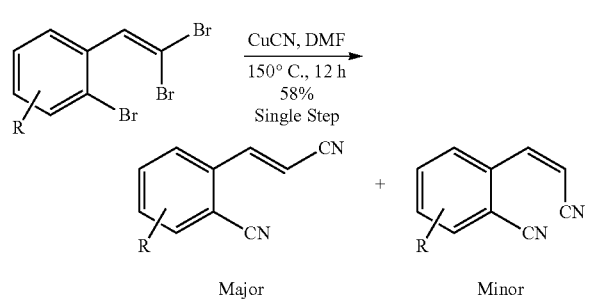

Wherein, R is selected from F, H, Br, OMe, OTs, OBn, NO$_2$, —O—CH$_2$—O—. Accordingly, in a preferred embodiment, a typical procedure is disclosed for the preparation of 3-(2-cyano-4,5-dimethoxyphenyl)acrylonitrile by refluxing a stirred solution of 1-bromo-2-(2,2-dibromovinyl)-4,5-dimethoxybenzene or 1-bromo-2-ethynyl-4,5-dimethoxybenzene in DMF with the addition of CuCN under N$_2$ atmosphere for 12 h (monitored by TLC). The reaction mixture is cooled to room temperature followed by workup of the reaction mixture to obtain crude products which can be purified by column chromatography to get 3-(2-cyano-4,5-dimethoxyphenyl)acrylonitrile in 63% yield.

The present invention discloses preparation of a library of compounds of cinnamonitrile derivatives by employing the process of the present invention. The reactants and the compounds obtained by the process of the invention is described herein below in tables 1.

TABLE 1

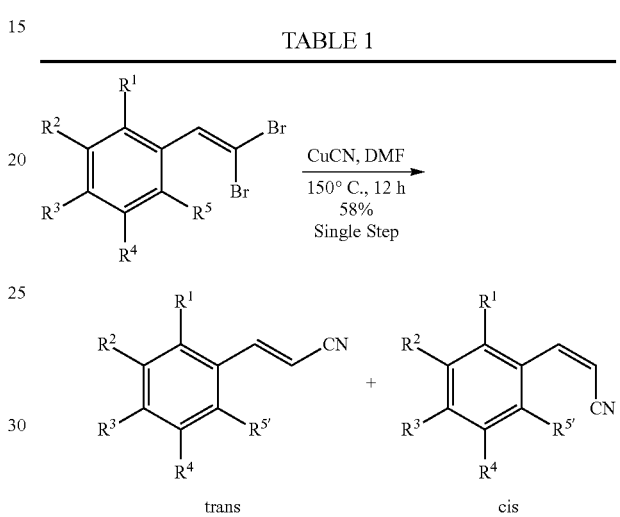

| S. no. | Reactants | | | | | | Products (trans/cis) | Yield$^a$ (%) |
|---|---|---|---|---|---|---|---|---|
| | R$^1$ | R$^2$ | R$^3$ | R$^4$ | R$^5$ | R$^{5'}$ | | |
| 1 | H | H | H | H | H | H | 4/1 | 53 |
| 2 | H | H | OMe | H | H | H | 3/1 | 52 |
| 3 | H | H | NO$_2$ | H | H | H | 4/1 | 86 |
| 4 | H | H | H | H | NO$_2$ | NO$_2$ | 4/1 | 88 |
| 5 | H | H | H | H | Br | CN | 10/1 | 56 |
| 6 | H | OMe | H | H | Br | CN | 4/1 | 73 |
| 7 | H | OMe | OMe | H | Br | CN | 3/1 | 82 |
| 8 | H | OMe | H | OMe | Br | CN | 3/1 | 71 |
| 9 | H | OMe | OMe | OMe | Br | CN | 4/1 | 73 |
| 10 | H | OBn | OMe | H | Br | CN | 4/1 | 57 |
| 11 | H | OBn | OBn | H | Br | CN | 4/1 | 71 |
| 12 | H | OTs | OMe | H | Br | CN | 4/1 | 52 |
| 13 | H | H | H | F | Br | CN | 3/1 | 63 |
| 14 | H | —O—CH$_2$—O— | | H | Br | CN | 3/1 | 71 |

$^a$Combined isolated yield after column chromatographic purification.

EXAMPLES

The following examples, which include preferred embodiments, will serve to illustrate the practice of this invention, it being understood that the particulars shown are by way of example and for purpose of illustrative discussion of preferred embodiments of the invention 1. General Information Solvents were purified and dried by standard procedures before use; petroleum ether of boiling range 60-80° C. was used. Melting points are uncorrected. Infrared spectra were recorded on Shimadzu FTIR-8400 spectrometer. $^1$H NMR and $^{13}$C NMR were recorded on Bruker AV-200, AV-400 & AV-500 NMR spectrometers, respectively. Elemental analysis was carried on a Carlo Erba CHNS-O analyzer. Purification was done using column chromatography (230-400 mesh).

2. Experimental Section

A General Experimental Procedure for the Preparation of Substituted Cinnamonitrile (2a-n)

Scheme 1: Synthesis of substituted cinnamonitrile (2a-n)

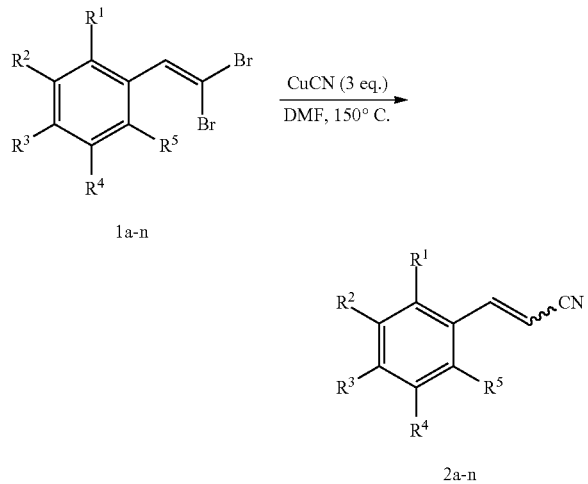

The dibromoolefines 1(a-n) (1 mmol) was taken in dry DMF (10 mL) and CuCN (3 mmol) was added to it and the entire solution refluxed under $N_2$ for 12 h (monitored by TLC). The reaction mixture was then cooled to room temperature, and diluted with water (30 mL) and EtOAc (25 mL). The organic layer was separated and the aqueous layer was extracted with EtOAc (3×20 mL). The combined organic extracts were washed with brine and dried over anhyd. $Na_2SO_4$ and concentrated under reduced pressure to give crude products which was purified by column chromatography [silica gel (230-400 mesh) and petroleum ether: EtOAc (7:3) as an eluent] to give substituted cinnamonitrile (a-i) in 73-82% yield.

3. Experimental Data

Cinnamonitrile (2a)

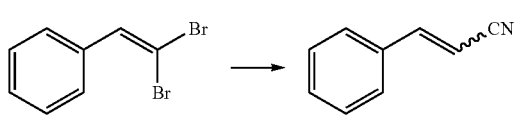 [SMILES: BrC(Br)=Cc1ccccc1 ; N#CC=Cc1ccccc1]

Yield: 72%; IR (CHCl$_3$, cm$^{-1}$): $\upsilon_{max}$ 965, 1030, 1107, 1244, 1301, 1601, 1624, 2217; $^1$H NMR (200 MHz, CDCl$_3$): δ 5.44 (d, J=12.2 Hz, 0.23H) Z-isomer, 5.87 (d, J=16.6 Hz, 1H) E-isomer, 7.11 (d, J=12.2 Hz, 0.42H) Z-isomer, 7.40-7.47 (m, 7H), 7.80 (dd, J=2.4, 3.6 Hz, 0.5H), 7.87; $^{13}$C-NMR (50 MHz, CDCl$_3$): δ 94.9, 96.3, 117.8, 127.2, 128.1, 128.7, 128.8128.9, 129.2, 130.7, 131.0, 133.4, 148.3, 150.2; Analysis: C$_9$H$_7$N requires C, 83.69; H, 5.46; N, 10.84. found: C, 83.49; H, 5.63; N, 10.24%.

3-(4-methoxyphenyl)acrylonitrile (2b)

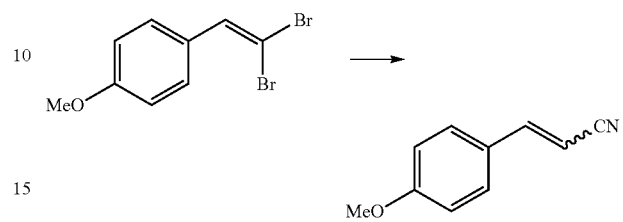

Yield: 78%; IR (CHCl$_3$, cm$^{-1}$): $\upsilon_{max}$ 985, 940, 1041, 1134, 1296, 1454, 1512, 1590, 2219; $^1$H NMR (200 MHz, CDCl$_3$): δ 3.84 (s, 3H), 3.85 (s, 3H), 5.28 (d, J=12.2, 1H) Z-isomer, 5.70 (d, J=16.5 Hz, 0.82H) E-isomer, 6.87-7.05 (m, 5H), 7.26 (d, J=3.0, 1H), 7.38 (d, J=8.84, 2H), 7.78 (d, J=8.84, 2H), $^{13}$C-NMR (50 MHz, CDCl$_3$): δ 55.1, 55.2, 91.6, 93.1, 114.0, 114.3, 126.1, 126.3, 128.8, 130.7, 147.7, 149.6, 161.4, 161.8; Analysis: C$_{10}$H$_9$NO requires C, 75.45; H, 5.70; N, 8.80. found: C, 75.65; H, 5.47; N, 8.71%.

3-(4-(methylthio)phenyl)acrylonitrile (2c)

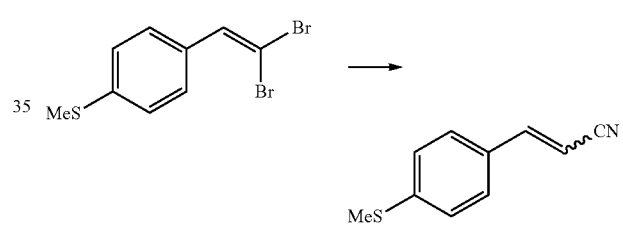

Yield: 74%; IR (CHCl$_3$, cm$^{-1}$): $\upsilon_{max}$ 752, 992, 1090, 1215, 1279, 1297, 1520, 2219; $^1$H NMR (200 MHz, CDCl$_3$): δ 2.50 (s, 5H), 5.35 (d, J=12.0 Hz, 0.48H) Z-isomer, 5.80 (d, J=16.6 Hz, 1H) E-isomer, 7.03 (d, J=12.0 Hz, 0.48H) Z-isomer, 7.18-7.36 (m, 6H), 7.72 (d, J=8.4 Hz, 1H); $^{13}$C-NMR (50 MHz, CDCl$_3$): δ 14.6, 93.3, 94.7, 117.3, 118.0, 124.6, 125.3, 125.5, 127.4, 129.1, 129.6, 129.7, 142.9, 143.1, 147.5, 149.4; Analysis: C$_{10}$H$_9$NS requires C, 68.53; H, 5.18; N, 7.99, S, 18.3 found: C, 68.69; H, 5.18; N, 7.56%.

3-(4-(trifluoromethyl)phenyl)acrylonitrile (2d)

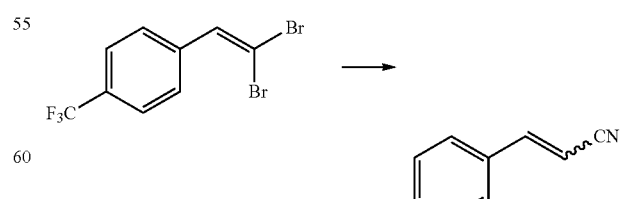

Yield: 73%; IR (CHCl$_3$, cm$^{-1}$): $\upsilon_{max}$ 816, 921, 1045, 1276, 1296, 2116; $^1$H NMR (200 MHz, CDCl$_3$): δ 5.60 (d, J=12.1 Hz, 0.82H) Z-isomer, 5.98 (d, J=16.6 Hz, 1H) E-isomer, 7.18

(d, J=12.1 Hz, 0.82H) Z-isomer, 7.43 (d, J=16.6 Hz, 1H) E-isomer, 7.57 (d, J=8.8 Hz 2H), 7.69 (t, J=6.57 Hz, 3H), 7.91 (d, J=8.8 Hz 2H); $^{13}$C-NMR (50 MHz, CDCl$_3$): δ 97.9, 99.2, 116.4, 117.1, 102.8, 125.6, 125.7, 125.8, 125.9, 126.0, 126.1, 127.5, 129.0, 136.6, 146.8, 148.5; Analysis: C$_{10}$H$_6$F$_3$N requires C, 60.92; H, 3.07; F, 28.91; N, 7.01 found: C, 60.71; H, 3.11; N, 6.96%.

3-(4-fluorophenyl)acrylonitrile (2e)

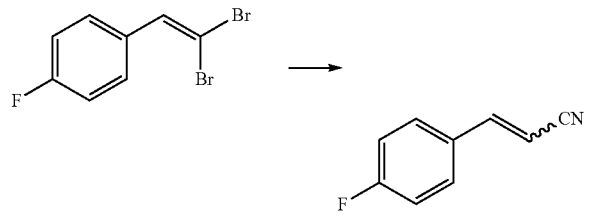

Yield: 76%; IR (CHCl$_3$, cm$^{-1}$): υ$_{max}$ 814, 912, 1011, 1064, 1246, 1512, 2219; $^1$H NMR (200 MHz, CDCl$_3$): δ 5.44 (d, J=12.2 Hz, 1H), Z-isomer, 5.80 (d, J=16.1 Hz, 0.84H) E-isomer, 7.05-7.17 (m, 5), 7.36 (d, J=16.1 Hz, 0.84H) E-isomer, 7.41-7.48 (m, 2H), 7.79-7.86 (m, 2H; $^{13}$C-NMR (50 MHz, CDCl$_3$): δ 97.5, 115.4, 117.0, 128.0, 130.8, 146.2, 162.1 Analysis: C$_9$H$_6$FN requires C, 73.46; H, 4.11; F, 12.91; N, 9.52. found: C, 73.62; H, 4.32; N, 9.42%.

3-(4-chlorophenyl)acrylonitrile (2f)

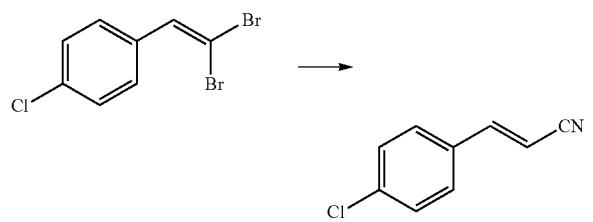

Yield: 81%; Colorless oil; IR (CHCl$_3$, cm$^{-1}$): υ$_{max}$ 772, 915, 1052, 1124, 1206, 1512, 2121; $^1$H NMR (200 MHz, CDCl$_3$): δ 5.83 (d, 1H, J=16.5 Hz), 7.3 (d, J=16.5 Hz, 1H), 7.38 (s, 4H; $^{13}$C-NMR (50 MHz, CDCl$_3$): δ 97.1, 117.5, 128.4, 129.3, 131.9, 137.2, 148.8; Analysis: C$_9$H$_6$ClN requires C, 66.07; H, 3.70; Cl, 21.6; N, 8.56. found: C, 66.21; H, 6.62; N, 8.32%.

3-(2-nitrophenyl)acrylonitrile (2g)

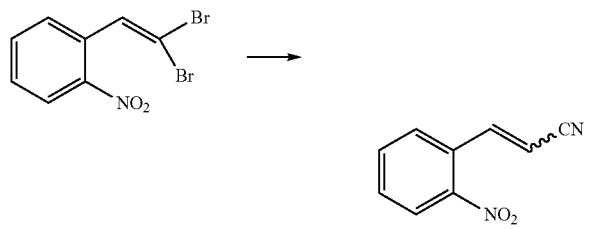

Yield: 88%; IR (CHCl$_3$, cm$^{-1}$): υ$_{max}$ 767, 1249, 1604, 1575, 1673, 2118; $^1$H NMR (200 MHz, CDCl$_3$): Z-isomer δ 5.72 (d, J=11.7 Hz, 1H), 7.61-7.90 (m, 4H), 8.22 (d, J=8.0 Hz, 1H); $^{13}$C-NMR (50 MHz, CDCl$_3$): δ 101.2, 115.7, 125.2, 129.5, 130.6, 130.9, 134.2, 146.3, 147.2; E-isomer; δ 5.85 (d, J=16.4 Hz, 1H), 7.56-7.76 (m, 3H), 7.96 (d, J=16.4 Hz, 1H), 8.13 (dd, J=1.5, 8.09 Hz, 1H); $^{13}$C-NMR (50 MHz, CDCl$_3$): δ 101.7, 116.7, 125.3, 128.6, 129.7, 131.2, 133.9, 146.4, 147.5; Analysis: C$_9$H$_6$N$_2$O$_2$ requires C, 66.07; H, 3.47; N, 16.09. found: C, 66.03; H, 3.13; N, 16.89%.

3-(4-nitrophenyl)acrylonitrile (2h)

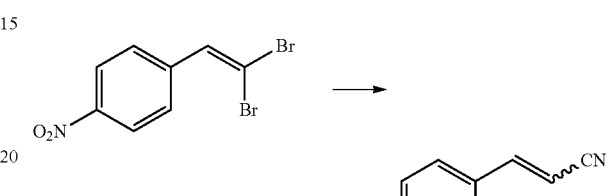

Yield: 86%; IR (CHCl$_3$, cm$^{-1}$): υ$_{max}$ 736, 853, 1249, 1604, 1546, 1665, 2116; $^1$H NMR (200 MHz, CDCl$_3$): Z-isomer δ 5.75 (d, J=11.6 Hz, 1H), 7.32 (d, J=11.6 Hz, 1H), 7.56 (d, J=8.1 Hz, 1H), 8.14 (d, J=8.1 Hz, 1H); $^{13}$C-NMR (50 MHz, CDCl$_3$): δ 99.2, 117.0, 122.2, 127.3, 141.3, 146.1, 147.6, 134.2, 146.3, 147.2; E-isomer; δ 6.05 (d, J=16.6 Hz, 1H), 7.47 (d, J=16.6 Hz, 1H), 7.63 (d, J=8.8 Hz, 2H), 8.28 (d, J=8.8 Hz, 2H); $^{13}$C-NMR (50 MHz, CDCl$_3$): δ 101.2, 116.7, 124.4, 128.1, 139.2, 147.6, 149.2; Analysis: C$_9$H$_6$N$_2$O$_2$ requires C, 66.07; H, 3.47; N, 16.09. found: C, 66.012; H, 3.32; N, 16.32%.

2-(2-cyanovinyl)-4,5-dimethoxybenzonitrile (2i)

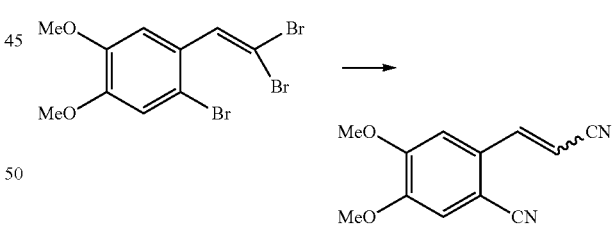

Yield: 82%; IR (CHCl$_3$, cm$^{-1}$): υ$_{max}$ 886, 927, 960, 1037, 1290, 1488, 1503, 2123; $^1$H NMR (200 MHz, CDCl$_3$): E-isomer; δ 3.95 (s, 3H), 3.98 (s, 3H), 5.98 (d, J=16.5 Hz, 1H), 7.01 (s, 1H), 7.09 (s, 1H), 7.65 (d, J=16.5 Hz, 1H); $^{13}$C-NMR (50 MHz, CDCl$_3$): δ 54.3, 93.7, 102.2, 106.7, 112.6, 115.1, 116.1, 128.2, 142.9, 149.2, 150.8; $^1$H NMR (200 MHz, CDCl$_3$): Z-isomer; δ 3.96 (s, 3H), 4.02 (s, 3H), 5.60 (d, J=12.1 Hz, 1H), 7.10 (s, 1H), 7.46 (d, J=12.1 Hz, 1H), 7.99 (s, 1H); $^{13}$C-NMR (50 MHz, CDCl$_3$): δ 56.3, 96.9, 106.0, 109.6, 114.1, 116.8, 130.3, 143.6, 150.9, 152.6; Analysis: C$_{12}$H$_{10}$N$_2$O$_2$ requires C, 67.28; H, 4.71; N, 13.08. found: C, 67.79; H, 4.12; N, 13.46%.

2-(2-cyanovinyl)-4-methoxybenzonitrile (2j)

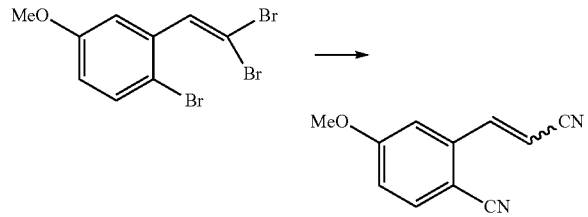

Yield: 73%; IR (CHCl$_3$): 547, 709, 767, 833, 856, 1023, 1247, 1597, 2211 cm$^{-1}$; $^1$H NMR (200 MHz, CDCl$_3$): Z-isomer; δ 3.94 (s, 3H), 5.70 (d, J=12.13 Hz, 1H), 7.01 (dd, J=2.53, 8.72 Hz, 1H), 7.49 (d, J=12.13 Hz, 1H), 7.63 (d, J=8.72 Hz, 1H), 7.86 (d, J=2.53 Hz, 1H); $^{13}$C NMR (CDCl$_3$): δ 55.80, 99.94, 104.95, 112.23, 116.10, 116.83, 117.88, 134.57, 137.77, 144.00, 162.91 $^1$H NMR (200 MHz, CDCl$_3$): δ 3.91 (s, 3H), 6.07 (d, J=16.54 Hz, 1H), 7.00 (dd, J=2.53, 8.59 Hz, 1H), 7.09 (d, J=2.53 Hz, 1H), 7.62 (d, J=16.54 Hz, 1H), 7.64 (d, 8.59 Hz, 1H); $^{13}$C NMR (CDCl$_3$): δ 55.79, 101.60, 104.12, 111.95, 116.67, 116.86, 135.25, 137.77, 145.53, 162.94; Analysis: C$_{11}$H$_8$N$_2$O$_1$ requires C, 71.73, H, 4.38, N, 15.21. found C, 70.18, H, 4.16, N, 14.97%.

6-(2-cyanovinyl)-2,3,4-trimethoxybenzonitrile (2k)

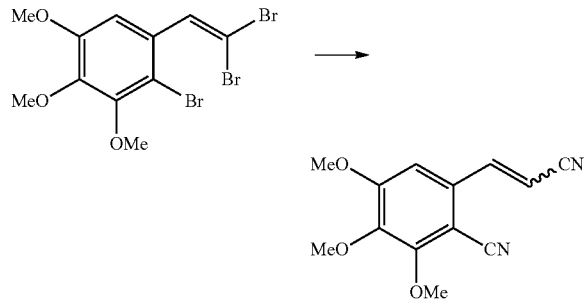

Yield: 71%; IR (CHCl$_3$, cm$^{-1}$): υ$_{max}$ 791, 845, 964, 1052, 1239, 1412, 1472, 1533, 1664, 2117; $^1$H NMR (200 MHz, CDCl$_3$): Z-isomer; δ 3.93 (s, 3H), 4.00 (s, 3H), 4.07, (s, 3H), 5.64 (d, J=12.2, 1H), 7.44 (d, J=12.2, 1H), 7.71 (s, 1H); $^{13}$C-NMR (50 MHz, CDCl$_3$): δ 56.4, 61.5, 61.8, 98.4, 101.1, 106.5, 114.1, 116.6, 132.0, 143.5, 143.7, 155.9, 157.3; $^1$H NMR (200 MHz, CDCl$_3$): E-isomer; δ 3.91 (s, 3H), 3.96 (s, 3H), 4.06, (s, 3H), 6.03 (d, J=16.5, 1H), 7.81 (s, 1H), 7.59 (d, J=16.5, 1H), $^{13}$C-NMR (50 MHz, CDCl$_3$): 56.3, 61.1, 61.7, 100.3, 104.6, 114.1, 116.9, 132.2, 143.6, 145.3, 155.8, 157.4 Analysis: C$_{13}$H$_{12}$N$_2$O$_3$ requires C, 63.93; H, 4.95; N, 11.47. found: requires C, 63.71; H, 4.51;

2-(2-cyanovinyl)-4,6-dimethoxybenzonitrile (2l)

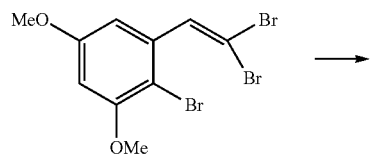

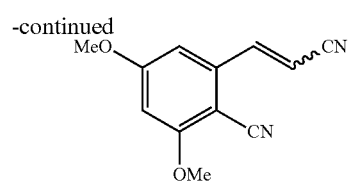

Yield: 71%; IR (CHCl$_3$, cm$^{-1}$): υ$_{max}$ 791, 845, 964, 1052, 1215, 1239, 1240, 1412, 1472, 1533, 1664, 2970, 3332, 3451; $^1$H NMR (200 MHz, CDCl$_3$): δ 3.90 (s, 3H), 3.94 (s, 3H), 6.09 (d, J=16.5, 1H), 6.52 (s, 1H), 6.64 (s, 1H), 7.61, (d, J=16.5, 1H); $^{13}$C-NMR (50 MHz, CDCl$_3$): δ 55.9, 56.3, 94.6, 100.1, 101.9, 103.2, 114.4, 116.7, 138.7, 145.8, 163.6, 164.2; Analysis: C$_{12}$H$_{10}$N$_2$O$_2$ requires C, 67.28; H, 4.71; N, 13.08. found: requires C, 67.61; H, 4.42; N, 13.15.

4,5-bis(benzyloxy)-2-((E)-2-cyanovinyl)benzonitrile (2m)

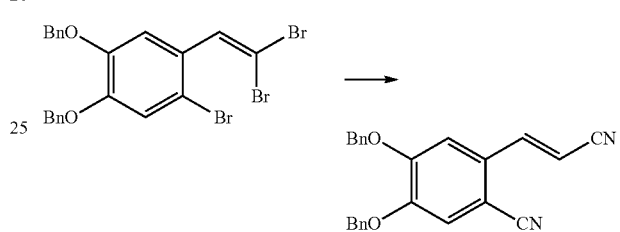

Yield: 71%; IR (CHCl$_3$, cm$^{-1}$): υ$_{max}$ 752, 991, 1091, 1244, 1279, 1296, 1454, 1462, 1512, 1590, 2219; $^1$H NMR (200 MHz, CDCl$_3$): δ 5.21 (s, 2H), 5.29 (s, 2H), 5.54 (d, J=12.2, 1H), 7.13 (s, 1H), 7.32-7.41 (m, 9H), 7.48, (d, J=7.3, 2H), 8.02, (s, 1H); $^{13}$C-NMR (50 MHz, CDCl$_3$): δ 71.0, 71.2, 97.0, 106.1, 111.7, 116.9, 127.2, 127.6, 128.4, 128.5, 128.7, 128.8 130.4, 135.5, 143.6, 150.5 152.4; Analysis: C$_{24}$H$_{18}$N$_2$O$_2$ requires C, 68.67; H, 4.95; N, 7.65. found: requires C, 68.54; H, 4.85; N, 7.12.

6-(2-cyanovinyl)benzo[d][1,3]dioxole-5-carbonitrile (2n)

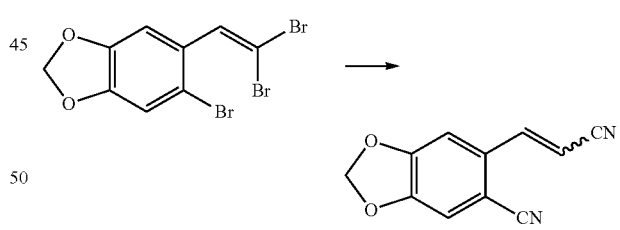

Yield: 71%; IR (CHCl$_3$, cm$^{-1}$): υ$_{max}$ 791, 841, 962, 1034, 1245, 1412, 2217; $^1$H NMR (200 MHz, CDCl$_3$): δ 5.62 (d, J=11.9, 1H), 6.17 (s, 2H), 7.10 (s, 1H), 7.45, (d, J=11.9, 1H) 7.84, (s, 1H); $^{13}$C-NMR (50 MHz, CDCl$_3$): δ 98.08, 103.1, 107.6, 11.8, 116.2, 116.5, 129.9, 132.4, 143.3, 149.7, 151.9; Analysis: C$_{11}$H$_6$N$_2$O$_2$ requires C, 66.67; H, 3.05; N, 14.14. found: requires C, 66.61; H, 3.49; N,

ADVANTAGES OF INVENTION

1. One pot process
2. Cheaper, safe and efficient
3. O-cyanocinnamonitrile and their esters have wide range of industrial applications for example in cosmetic industry.

4. Broad substrate scope and good functional group tolerance
5. Less amount of effluent generate

We claim:

1. A one pot, single step process for the preparation of compound of general formula A and its isomers,

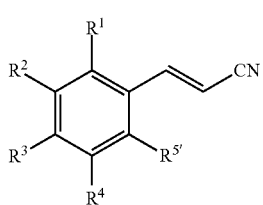

Formula A starting from compounds of formula I,

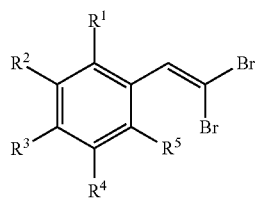

Formula I wherein, $R^1$ is hydrogen;
$R^2$ is selected from H, OMe, OTs, OBn;
$R^3$ is selected from H, OMe, OTs, OBn, $NO_2$;
$R^4$ is selected from H, OMe, F;
$R^5$ is selected from H, $NO_2$, Br;
$R^{5'}$ is selected from H, $NO_2$, CN;
$R^2$ and $R^3$ can together be selected as —O—$CH_2$—O—;

comprising the steps of reacting compound of formula I with CuCN in DMF, under reflux in presence of $N_2$ atmosphere to obtain the desired compound of formula A in the range of 50-90% yield.

2. The process according to claim 1, wherein said compound of formula I and CuCN are in the ratio of 1:2 to 1:3.

3. The process according to claim 1, wherein said isomers of compound of formula A are trans and cis isomers in the ratio of 3:1 to 10:1.

4. The process according to claim 1, wherein the reaction is carried out at a temperature ranging from 140 to 160° C.

5. The process according to claim 1, wherein the reaction is carried out for a time ranging from 10 to 15 hours.

* * * * *